United States Patent
Yamamoto et al.

(10) Patent No.: US 6,930,205 B2
(45) Date of Patent: Aug. 16, 2005

(54) PROCESS FOR PREPARING AMINOSTILBENE DERIVATIVES

(75) Inventors: Takashi Yamamoto, Kawasaki (JP); Hiroyuki Matsueda, Kawasaki (JP); Masaki Naito, Kawasaki (JP); Isao Arai, Kawasaki (JP); Masanobu Yatagai, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/740,543

(22) Filed: Dec. 22, 2003

(65) Prior Publication Data

US 2004/0176642 A1 Sep. 9, 2004

Related U.S. Application Data

(63) Continuation of application No. PCT/JP02/06174, filed on Jun. 20, 2002.

(30) Foreign Application Priority Data

Jun. 22, 2001 (JP) ......................................... 2001-190117

(51) Int. Cl.$^7$ ............................................. C07C 211/43
(52) U.S. Cl. ....................................................... 564/305
(58) Field of Search ............................................ 564/305

(56) References Cited

U.S. PATENT DOCUMENTS

| | | |
|---|---|---|
| 5,731,353 A | 3/1998 | Ohsumi et al. |
| 5,886,025 A | 3/1999 | Pinney |
| 6,162,930 A | 12/2000 | Pinney et al. |
| 2001/0034454 A1 | 10/2001 | Pinney et al. |

FOREIGN PATENT DOCUMENTS

| | | |
|---|---|---|
| EP | 0 641 767 | 9/1994 |
| JP | 08-283216 | 10/1996 |
| WO | WO 98/39323 | 9/1998 |

OTHER PUBLICATIONS

Pinney, K.G., et al., "Synthesis and Biological Evaluation of Aryl Azide Derivatives of Combretastatin A–4 as Molecular Probes for Tubulin," *Bioorganic & Medicinal Chemistry*, vol. 8, No. 10, pp. 2417–2425 (2000).

Cushman, Mark, et al., "Synthesis and Evaluation of Stilbene and Dihydrostilbene Derivatives as Potential Anticancer Agents that Inhibit Tubulin Polymerization," *J. Med. Chem.*, 1991, vol. 34, pp. 2579–2588.

Ohsumi, Koji, et al., "Novel Combretastatin Analogues Effective Against Murine Solid Tumors: Design and Structure—Activity Relationships," *J. Med. Chem.*, (1998), vol. 41, pp. 3022–3032.

Gowda, D.C., et al., Catalytic Transfer Hydrogenation of Aromatic Nitro Compounds by Employing Ammonium Formate and 5% Platinum on Carbon, *Synthetic Communications*, vol. 30, No. 20, pp. 3639–3644 (2000).

Variyar, Prasad S., et al., "Synthesis of 3,4–dihydroxy–6–(N–ethyl–amino)benzamide, a New Phenolic Compound Isolated From Green Pepper", *Indian Journal of Chemistry*, vol. 34B, Oct. 1995, pp. 911–913.

*Primary Examiner*—Kamal Saeed
(74) *Attorney, Agent, or Firm*—Oblon, Spivak, McClelland, Maier & Neustadt, P.C.

(57) ABSTRACT

The present invention relates to a novel process for preparing an aminostilbene derivative, which is important as an active component of anticancer drugs or an intermediate for preparation thereof, as well as methods of producing the same.

21 Claims, No Drawings

PROCESS FOR PREPARING AMINOSTILBENE DERIVATIVES

CROSS-REFERENCE TO RELATED APPLICATIONS

The present application is a continuation application of International application PCT/JP02/06174, filed on Jun. 20, 2002, which claims priority to Japanese Application No. 2001-190117, filed on Jun. 22, 2001, which are hereby incorporated by reference in their entirety.

BACKGROUND OF THE INVENTION

1. Field of the Invention

The present invention relates to a novel process for preparing an aminostilbene derivative, which is important as an active component of anticancer drugs or an intermediate for preparation thereof. The present invention further provides a process for producing an aminostilbene derivative with an enhanced efficiency and industrial convenience as compared to the conventional techniques in the art.

2. Discussion of the Background

Combretastatins, including cis-stilbene as the basic skeleton, are provided with intensive mitosis inhibiting activity and intensive cytotoxicity. Therefore, investigations are on going for the development of anticancer drugs using a derivative thereof as the active (effective) component. In particular, development of an anticancer drug is now desired for the compounds represented by the following general formulas (3) or (4), since these compounds have low toxicity and high therapeutic efficacy (refer to: Japanese Patent Kokai Publications JP-A-7-228,558 and JP-A-8-301,831).

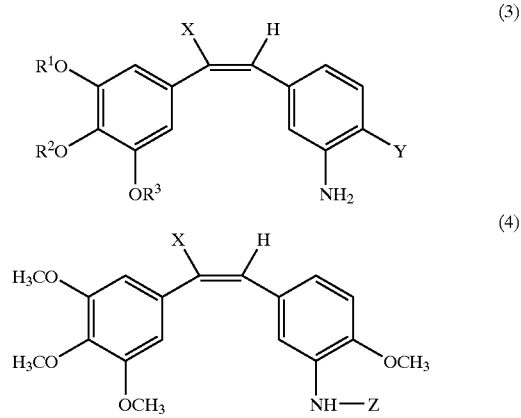

In the above formulas (3) and (4), each of $R^1$, $R^2$ and $R^3$ independently represents an alkyl group having 1–3 carbon atoms, X represents a hydrogen atom or a nitrile group, Y represents an alkoxy group having 1–3 carbon atoms, an alkyl group having 1–6 carbon atoms or a halogen atom and Z represents an amino acid acyl group, respectively.

The compounds represented by formulas (3) or (4) have an amino group or a substituted amino group on the benzene ring of phenyl group. A proposal has been set forth for a method of converting a nitro group into an amino group by reduction as a process for preparation these compounds, for example, the reducing method using zinc-acetic acid (refer to: Japanese Patent Kokai Publication JP-A-7-228,558) and the reducing method using sodium dithionite (Bioorganic and Medicinal Chemistry, vol. 8, 2000, page 2417). However, in the zinc-acetic acid method, it is necessary to use zinc in an extremely large excess based on the nitro compound, which is the substrate in the reaction. Consequently, a large amount of zinc is yielded as waste matter further accompanied with, e.g., exothermic decomposing property thereof so that there are many of problems in the environmental consideration and safety consideration for industrialization. In addition, in the sodium dithionite method, sodium dithionite in a large excess is used and the resultant yield is not sufficient.

It is desirable to adopt a stoichiometric reaction, or more desirably to adopt a catalytic reaction, for establishing a production process that yields reduced quantities of waste matter. However, it is not easy to selectively reduce only the nitro groups without any affect on the double bond under catalytic reduction conditions as it is usual for such a condition to induce reduction of the carbon-carbon double bonds to single bonds or cis-trans isomerization of carbon-carbon double bonds. In other words, although more exemplifications of the preparation of an aminostilbene derivative from a nitrostilbene derivative by the catalytic reaction that include little description on the stereochemistry of double bonds may be found, there are report articles on the hydrogenation method using a platinum oxide catalyst (refer to J. Am. Chem. Soc., 1940, vol. 62, page 1211), on the hydrogenation method using platinum on carbon (refer to Japanese Patent Kokai Publication JP-A-6-172,295), and so forth. The present inventors have confirmed that the object compound of the present invention is formed merely in a trace amount and the isomerization and reduction of the double bond are mainly induced with predominance so that these methods are industrially not useful (refer to aftermentioned Comparative Examples) when these methods are applied using the compound used as the starting material in the present invention.

Accordingly, there remains a critical need and a demand for a method of selectively converting the nitro group of the above nitrostilbene derivative into an amino group with high efficiency.

SUMMARY OF THE INVENTION

It is an object of the present invention to provide a process of reducing a nitrostilbene derivative for converting into an aminostilbene derivative, developing a selective reducing method for nitro groups which yields less amount of waste matters and has high selectivity consequently to provide a method of industrially producing an aminostilbene derivative which is important as an active component of anticancer drugs or as an intermediate for preparation thereof with advantageousness.

It is an object of the present invention to provide a method for preparing an aminostilbene derivative of formula (2):

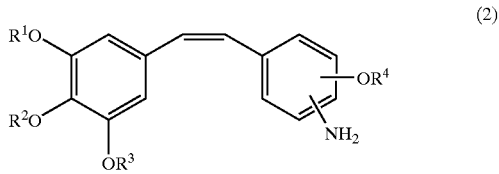

wherein each of $R^1$, $R^2$, $R^3$ and $R^4$ independently represents an alkyl group having 1–3 carbon atoms and the linking sites of $OR^4$, $NO_2$ and $NH_2$ on the benzene ring are optional comprising reacting a nitrostilbene derivative represented by formula (1) with formic acid and/or a formate salt in the presence of a noble metal catalyst

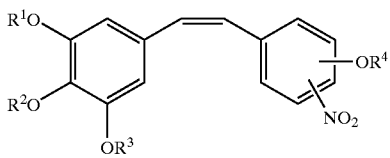

(1)

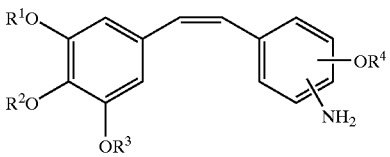

(2)

wherein each of $R^1$, $R^2$, $R^3$ and $R^4$ independently represents an alkyl group having 1–3 carbon atoms and the linking sites of $OR^4$, $NO_2$ and $NH_2$ on the benzene ring are optional.

The above objects highlight certain aspects of the invention. Additional objects, aspects and embodiments of the invention are found in the following detailed description of the invention.

DETAILED DESCRIPTION OF THE INVENTION

Unless specifically defined, all technical and scientific terms used herein have the same meaning as commonly understood by a skilled artisan in organic chemistry, pharmacology, pharmaceuticals, pharmaceutical formulations, and the medical sciences.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will control. Further, the materials, methods, and examples are illustrative only and are not intended to be limiting, unless otherwise specified.

The present inventors have performed numerous investigations to ascertain a method of reducing nitro groups, particularly a catalytic reduction method, as a substitution for the zinc-acetic acid method with an object of solving the above-stated problems with the same. The present inventors have found high selectivity is obtained by the reduction using a noble metal catalyst and formic acid or a formate salt as the hydrogen donor thus to attain completion of the present invention standing on this knowledge.

The present invention provides a process for preparing an aminostilbene derivative represented by the following general formula (2) in which a nitrostilbene derivative represented by the following general formula (1) is reacted with formic acid and/or a formate salt in the presence of a noble metal catalyst.

In the present invention the aminostilbene derivative may also be in the form of a salt.

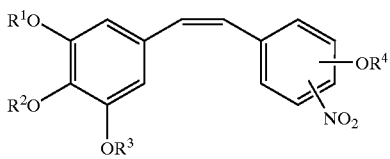

(1)

In formulas (1) and (2) above, each of $R^1$, $R^2$, $R^3$ and $R^4$ independently represents an alkyl group having 1–3 carbon atoms and the linking sites of the $OR^4$, $NO_2$ and $NH_2$ on the benzene ring are indicated as being optional. In a preferred embodiment, at least one of $R^1$, $R^2$, $R^3$ and $R^4$ represents a methyl group or, more preferably, each of $R^1$, $R^2$, $R^3$ and $R^4$ represents respectively a methyl group.

The linking sites of $OR^4$, $NO_2$ and $NH_2$ on the benzene ring are indicated as being optional but, since the nitro group in the derivative represented by the above formula (1) is reduced to an amino group by the reaction, the site of amino group on the benzene ring of the derivative represented by the above formula (2) corresponds to the site of nitro group on the benzene ring of derivative represented by the above formula (1). Similarly, since, with respect to the site on the benzene ring of $OR^4$, there is no change in the sites thereof between the times of before and after the reaction, it is regarded that linking is made at the same sites in relation to the linking site of substituted vinyl group on the benzene ring of derivatives before the reaction indicated by formula (1) and after the reaction indicated by formula (2).

In another embodiment of the present invention, $OR^4$ on the benzene ring is linked to the 4-position and the $NO_2$ is linked to the 3-position with respect to the linking site of substituted vinyl group. In this case, the prepared derivative has an $OR^4$ linked to the 4-position and an $NH_2$ linked to the 3-position on the benzene ring to the linking site of substituted vinyl group in the above formula (2).

With respect to the noble metal catalyst, it is preferable to use a platinum catalyst (such as platinum on carbon) or a palladium catalyst (such as palladium on carbon).

Although formic acid or a formate salt is used as the hydrogen donor in the reduction, it is more preferable to use a formate salt such as ammonium formate.

In the above reaction, it is also possible to prepare the aminostilbene derivative in the form of a free base to be isolated as the objective substance. It is also possible to subject the free base further to a procedure of salt-formation according to necessity for preparing a salt of the aminostilbene derivative to obtain it as the objective substance. Accordingly, even in the cases of appending any one or more procedures for obtaining an industrially required product through a salt-formation procedure, a desalting procedure, an isolating procedure, a purification procedure, and/or mixtures of these procedures can be employed. Further, the present invention can be comprehended as incorporating the above additional procedure(s) on condition of including the procedure of reduction as the above-mentioned characteristic part of present invention, or on condition of not impairing the object of attaining the effect of present invention.

In the present invention, it is possible to list the following procedures as the particularly typical reacting mode:

a. A process for preparing (Z)-2-methoxy-5-[2-(3,4,5-trimethoxyphenyl)vinyl]aniline or a salt thereof after reacting (Z)-3,4,4',5-tetramethoxy-3'-nitrostilbene with a formate salt in the presence of a platinum catalyst.

b. A process for preparing (Z)-2-methoxy-5-[2-(3,4,5-trimethoxyphenyl)vinyl]aniline or a salt thereof after reacting (Z)-3,4,4',5-tetramethoxy-3'-nitrostilbene with a formate salt in the presence of a palladium catalyst.

It is possible to apply common desalting procedures or common procedures of salt-formation in the preparation of a free base or a salt.

An explanation is given below on the mode of practicing the present invention.

In the present invention, the starting material used in the reduction of nitro groups should be a specific nitrostilbene derivative represented by the above general formula (1).

No particular difficulty accompanies preparation of the nitrostilbene derivative represented by the above general formula (1) to allow easy preparation of them by application of the prior art technology (refer to e.g., Japanese Patent Kokai Publication JP-A-7-228,558). For instance, the following process thereof can exemplify the preparation method:

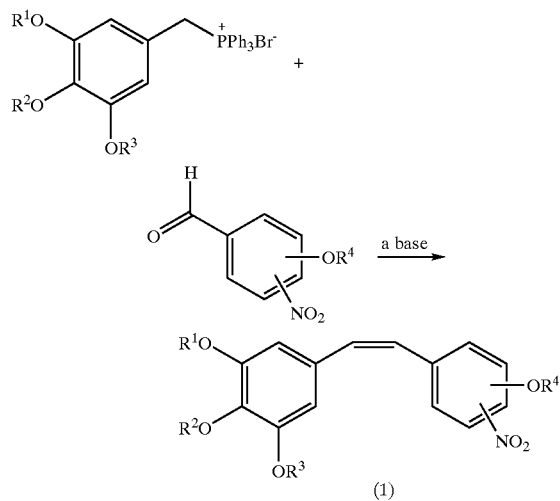

In formulas (1) and (2), each of $R^1$, $R^2$, $R^3$ and $R^4$ independently represents an alkyl group having 1–3 carbon atoms but it is as more preferable to choose methyl groups as possible with particular preference to choosing methyl groups for all of $R^1$–$R^4$.

As the starting material, it is preferable to use a derivative in which the $OR^4$ is linked to the 4-position and the $NO_2$ is linked to the 3-position on the benzene ring to the linking site of substituted vinyl group. In this case, the substance produced through the reduction in the present invention is a derivative in which the $OR^4$ is linked to the 4-position and the $NH_2$ is linked to the 3-position on the benzene ring to the linking site of substituted vinyl group in the above general formula (2).

There is no particular restriction for the noble metal catalyst used in the present invention. It is possible to adopt a catalyst containing a noble metal known as a reducing catalyst and also a noble metal catalyst of reducing character that will be hereafter developed. For instance, it is possible to exemplify by platinum catalysts, palladium catalysts, ruthenium catalysts, rhodium catalysts and the like. More specifically, the platinum catalyst is exemplified by platinum on carbon (Pt—C), platinum on alumina, platinum oxide, platinum black and the like, the palladium catalyst is exemplified by palladium on carbon (Pd—C), palladium on alumina, palladium on calcium carbonate, palladium on barium sulfate, palladium hydroxide on carbon, palladium black and the like, the ruthenium catalyst is exemplified by ruthenium on carbon (Ru—C), ruthenium on alumina and the like and the rhodium catalyst is exemplified by rhodium oh carbon, rhodium on alumina and the like.

Among the noble metal catalysts, the platinum catalysts and palladium catalysts are preferably used, among the platinum catalysts the platinum on carbon is preferably used, and among the palladium catalysts the palladium on carbon is used preferably.

With respect to the amount of noble metal catalyst to be used, it is possible to use the noble metal catalyst in an amount, based on the nitrostilbene derivative as the starting material, ranging from approximately 0.1–10 mole %, preferably approximately 0.2–5 mole %, more preferably 0.3–3 mole %. In a case in which the starting material is intermingled with any of impurities having nitro groups, for example with an isomer of the above starting material, it is preferable to determine the amount to use by taking the reduction of this/these impurity(ies) into consideration since the nitro groups in the impurities are also reduced. For instance, it is possible to use the catalyst within the range of above numerical value to the whole amount of derivatives containing nitro groups in addition to the above starting material.

In the present invention, the hydrogen donor used in the reduction is preferably formic acid and/or a formate salt. The formate salt is preferably exemplified by ammonium formate, sodium formate and the like, but it is also possible to generate a formate salt in the reaction system by the use of formic acid and a basic component and to use also a mixture of formic acid and a formate salt. Furthermore, regarding the formate salt, it is also possible to use it in the form of hybrid salt of several species not limitedly to a single salt.

With respect to the amount of formic acid and/or a salt thereof for use as the hydrogen donor, the amount of formic acid and/or the salt may be within the range of approximately 200–700 mole %, preferably of approximately 220–500 mole %, and more preferably approximately 250–400 mole % to the above nitrostilbene derivative as the starting material, but it is preferable for suppressing remaining of the nitro compound and side reactions to use it in an amount of approximately 300 mole % (i.e., 250–350 mole %). As stated above, when the starting material is intermingled with impurities containing nitro groups, it is preferable to determine the use amount of above formate salt and so forth with consideration on the amounts of these impurities.

The reduction in the present invention is practiced in a solvent. The solvent may be exemplified by alcohols such as methanol, ethanol and the like, esters including acetate esters such as ethyl acetate, isopropyl acetate and the like, ethers such as tetrahydrofuran and the like, nitriles such as acetonitrile and the like and water, and it is also possible to use a solvent mixture of the same. The range of temperature applied to the reduction may be approximately from 0° C. to the boiling temperature of reaction mixture with preference to approximately 10–50° C. or with specific preference to approximately 20–45° C.

In the present invention, it is possible to use an additive, though not being indispensable, for attaining effective progression of the reduction or for suppressing the side reactions. The additive may include various bases such as amines, ammonia, inorganic bases and the like.

The aminostilbene derivative obtained by the reduction can be isolated after purification by conventional methods such as extraction, crystallization, chromatography and the like succeeding to separation of the catalyst. It is also possible to isolate the aminostilbene derivative in the form of a salt with an acid. Otherwise, in the cases in which the reaction is further continued using the aminostilbene derivative as an intermediate, it is also possible to use it in the succeeding procedure as it is without isolation or after partial purification. In the present invention, since the above selective reduction of nitro groups is the characteristic feature thereof, all of the matters containing the objective substance represented by the above formula (2) or salts thereof, and obtained through such reduction reaction, correspond to the matter produced or prepared by the present invention irrespective of the form thereof including a solution, a mixture, a purified substance and the like.

In the cases in which purification is performed in the form of a salt, it is recommended to prepare the salt by applying the conventional procedures of salt formation followed by isolation thereof. Further, it is also possible to obtain the objective substance in the form of a free base by preparing in the form of a salt followed further by application of the conventional desalting procedures and the present invention covers all of such processes in combination with the above reduction.

Industrial production is conveniently practiced with high efficiency for various specific aminostilbene derivatives or salt(s) thereof such as (Z)-3,4,4',5-tetramethoxy-3'-aminostilbene and the like, which are important as an active component of anticancer drugs or intermediates for production thereof, by the selective reduction of mere nitro group through the reaction of a specific nitrostilbene derivative such as (Z)-3,4,4',5-tetramethoxy-3'-nitrostilbene or the like with formic acid and/or a formate salt in the presence of a noble metal catalyst such as platinum catalysts, palladium catalysts or the like.

Having generally described this invention, a further understanding can be obtained by reference to certain specific examples, which are provided herein for purposes of illustration only, and are not intended to be limiting unless otherwise specified.

EXAMPLES

Example 1

Synthesis of (Z)-2-methoxy-5-[2-(3,4,5-trimethoxyphenyl)vinyl]aniline

A solution was prepared by dissolving (Z)-3,4,4',5-tetramethoxy-3'-nitrostilbene (termed also as "raw material 5") (8.63 g, 25.0 mmol) represented by formula (5) below in acetonitrile (100 ml) succeeded by addition of ammonium formate (5.21 g, 82.6 mmol, 330 mole % to the above nitrostilbene derivative (raw material 5)) and 5% platinum on carbon (water-content: 60.91%, 4.99 g, 0.50 mmol as platinum) to be subjected to a reaction at 30° C. for 20.5 hours in an argon atmosphere. At the conclusion of the reaction, the catalyst and the insoluble matter were separated by filtration followed by quantitative analysis employing high-performance liquid chromatography (HPLC) for the obtained filtrate.

It was confirmed that the reaction product obtained contained: (a) (Z)-2-methoxy-5-[2-(3,4,5-trimethoxyphenyl)vinyl]aniline (represented by formula (6) below and termed herein as "objective substance 6") as the objective substance (6.49 g, 20.6 mmol, 82%); (b) (E)-2-methoxy-5-[2-(3,4,5-trimethoxyphenyl)vinyl]aniline (represented by formula (7) below and termed herein as "by-product 7") as a by-product (0.39 g, 1.24 mmol, 5.0%); and (c) 2-methoxy-5-[2-(3,4,5-trimethoxyphenyl)ethyl]aniline (represented by formula (8) below and termed also as "by-product 8") as a by-product (0.34 g, 1.07 mmol, 4.3%). By-product formation of 2-(4-methoxy-3-nitrophenyl)-1-(3,4,5-trimethoxyphenyl)ethane (represented by formula (9) below and termed also as "by-product 9") was not observed.

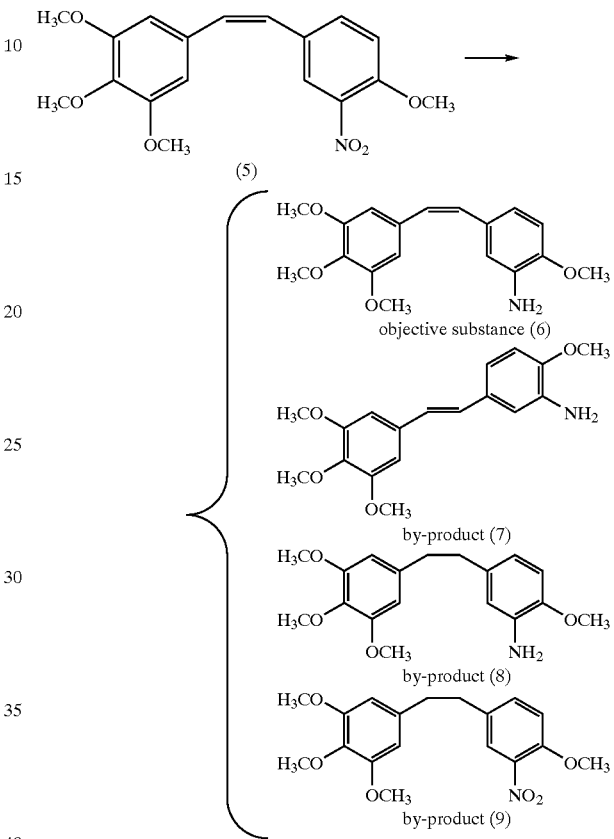

Example 2

Synthesis of (Z)-2-methoxy-5-[2-(3,4,5-trimethoxyphenyl)vinyl]aniline

A reaction was conducted in the similar manner to that in Example 1. Specifically, the reaction was conducted for 19.5 hours while changing the amount of ammonium formate to 300 mole % to the nitrostilbene derivative (5) (raw material 5) as the starting material. At the conclusion of the reaction, quantitative analysis was performed by HPLC on the filtrate obtained by separation of the catalyst and the insoluble matter by filtration to determine the yields of formed products as 82% for the objective substance 6 (the aminostilbene derivative represented by the above formula (6)) and 1.2%, 1.5% and 1.8% respectively for the by-product 7, by-product 8 and by-product 9 though 10% of the raw material 5 remained.

Example 3

Synthesis of (Z)-2-methoxy-5-[2-(3,4,5-trimethoxyphenyl)vinyl]aniline

A solution was prepared by dissolving (Z)-3,4,4',5-tetramethoxy-3'-nitrostilbene (raw material 5) represented by the above formula (5) (5.0 g, 14.5 mmol in total including 14% of trans-isomer) in acetonitrile (58 mL) followed by addition of ammonium formate (95%, 2.88 g, 43.4 mmol, 300 mole % to the total of the above nitrostilbene derivative (raw material 5) and the trans-isomer thereof) and 10% palladium on carbon (water-content: 51.3%, 637 mg, 0.29 mmol as palladium) to be subjected to a reaction at 30° C. for 24 hours. At the conclusion of the reaction, the reaction solution was analyzed by HPLC. The resultant peak areas shown at a detection wavelength of 242 nm were 69%, 14%, 1.4%, 0.6%, 12% and 1.9%, respectively, for the objective substance (Z)-2-methoxy-5-[2-(3,4,5-trimethoxyphenyl) vinyl]aniline (objective substance 6; represented by the above formula (6)), by-products (E)-2-methoxy-5-[2-(3,4,5-trimethoxyphenyl)vinyl]aniline (by-product 7; represented by the above formula (7)), 2-methoxy-5-[2-(3,4,5-trimethoxyphenyl)ethyl]aniline (by-product 8; represented by the above formula (8)) and 2-(4-methoxy-3-nitrophenyl)-1-(3,4,5-trimethoxyphenyl)ethane (by-product 9; represented by the above formula (9)), the nitrostilbene derivative as the starting material (raw material 5; represented by the above formula (5)) and the trans-isomer of raw material 5. It was understood that, in consideration that the starting material contained 14% of the trans-isomer, isomerization from the cis-isomer to the trans-isomer was trifling during the reaction.

Example 4

Synthesis of (Z)-2-methoxy-5-[2-(3,4,5-trimethoxyphenyl)vinyl]aniline

A solution was prepared by dissolving (Z)-3,4,4',5-tetramethoxy-3'-nitrostilbene (raw material 5) represented by the above formula (5) (5.0 g, 14.5 mmol in total including 14% of the trans-isomer) in acetonitrile (58 mL) followed by addition of 10% palladium on carbon (water-content: 51.3%, 633 mg, 0.29 mmol as palladium), aqueous ammonia (29%, 0.85 g, 14.5 mmol) and ammonium formate (95%, 2.88 g, 43.4 mmol, 300 mole % to the total of the above nitrostilbene derivative (raw material 5) and the trans-isomer thereof) to be subjected to a reaction at 30° C. for 28 hours. At the conclusion of the reaction, the catalyst and the insoluble matter were separated by filtration followed by analysis of the filtrate by HPLC. The resultant peak areas shown at a detection wavelength of 242 nm were 72%, 13%, 1.3%, 0.6%, 11% and 1.6%, respectively, for the (Z)-2-methoxy-5-[2-(3,4,5-trimethoxyphenyl)vinyl]aniline as the objective substance (objective substance 6; represented by the above formula (6)), by-products (E)-2-methoxy-5-[2-(3,4,5-trimethoxyphenyl)vinyl]aniline (by-product 7; represented by the above formula (7)), 2-methoxy-5-[2-(3,4,5-trimethoxyphenyl)ethyl]aniline (by-product 8; represented by the above formula (8)) and 2-(4-methoxy-3-nitrophenyl)-1-(3,4,5-trimethoxyphenyl)ethane (by-product 9; represented by the above formula (9)), the nitrostilbene derivative as the starting material (raw material 5), and the trans-isomer of the raw material 5. In consideration that the starting material contained 14% of the trans-isomer, it was understood that isomerization from the cis-isomer to the trans-isomer was trifling during the reaction.

Example 5

Synthesis of (Z)-2-methoxy-5-[2-(3,4,5-trimethoxyphenyl)vinyl]aniline

To the (Z)-3,4,4',5-tetramethoxy-3'-nitrostilbene represented by the above formula (5) (raw material 5) (173 mg, 0.50 mmol) 10% palladium on carbon (water-content: 52.4%, 25.8 mg, 0.01 mmol as palladium), ammonium formate (95%, 232 mg, 3.5 mmol, 700 mole % to the above starting material; nitrostilbene derivative (raw material 5)), ethyl acetate (7.5 ml) and pyridine (0.79 mg, 0.01 mmol) were added to be reacted at 43° C. for 5 hours. At the conclusion of the reaction, the reaction solution was analyzed by HPLC. The resultant peak areas shown at a detection wavelength of 242 nm were 74%, 7.7%, 7.1%, 6.4%, 3.6% and 0.1%, respectively, for the objective substance (Z)-2-methoxy-5-[2-(3,4,5-trimethoxyphenyl)vinyl] aniline (objective substance 6; represented by the above formula (6)), by-products (E)-2-methoxy-5-[2-(3,4,5-trimethoxyphenyl)vinyl]aniline (by-product 7; represented by the above formula (7)), 2-methoxy-5-[2-(3,4,5-trimethoxyphenyl)ethyl]aniline (by-product 8; represented by the above formula (8)) and 2-(4-methoxy-3-nitrophenyl)-1-(3,4,5-trimethoxyphenyl)ethane (by-product 9; represented by the above formula (9)), the nitrostilbene derivative as the above starting material (raw material 5) and the trans-isomer of raw material 5.

Example 6

Synthesis of (Z)-2-methoxy-5-[2-(3,4,5-trimethoxyphenyl)vinyl]aniline

A solution was prepared by dissolving (Z)-3,4,4',5-tetramethoxy-3'-nitrostilbene (raw material 5) (8.63 g, 25.0 mmol) in acetonitrile (100 ml) succeeded by addition of ammonium formate (5.21 g, 82.6 mmol, 330 mole % to the above nitrostilbene derivative (raw material 5)), 5% platinum on carbon (water-content: 60.91%, 4.99 g, 0.50 mmol as platinum) and aqueous ammonia (28%, 1.69 ml, 25 mmol) to be reacted at 30° C. for 23 hours in an argon atmosphere. At the conclusion of the reaction, the catalyst and the insoluble matter were separated by filtration and the filtrate was subjected to quantitative analysis by HPLC. Formation of the objective substance, (Z)-2-methoxy-5-[2-(3,4,5-trimethoxyphenyl)vinyl]aniline (objective substance 6; represented by the above formula (6)) (6.52 g, 20.7 mmol, 83%), was confirmed, as was formation of a by-product (E)-2-methoxy-5-[2-(3,4,5-trimethoxyphenyl)vinyl]aniline (by-product 7; represented by the above formula (7)) (0.55 g, 1.73 mmol, 6.9%) and a by-product 2-methoxy-5-[2-(3,4,5-trimethoxyphenyl)ethyl]aniline (by-product 8; represented by the above formula (8)) (0.52 g, 1.63 mmol, 6.5%). Formation was not observed for the by-product 2-(4-methoxy-3-nitrophenyl)-1-(3,4,5-trimethoxyphenyl)ethane (by-product 9; represented by the above formula (9)).

Comparative Examples 1–4

In order to make comparison with the present invention, experiments were similarly performed by applying the catalyst systems, reducing conditions and common conditions for catalytic reduction described in preceding literatures as the prior art method to obtain Comparative Examples 1–4.

Table 1 (below) provides the results obtained in the above Examples and in the Comparative Examples. As can be seen in the results of Table 1, it was determined that the reduction was efficiently advanced by the method of the present invention to form the objective derivative in a high yield. In contrast, the method of the prior art resulted in either a less favorable reduction (refer to the Comparative Example 4) or a significant increase in by-product formation (refer to the Comparative Examples 1–3).

Details of the descriptions in Table 1 are as shown in the following:

raw material 5: the nitrostilbene derivative represented by the above formula (5);

The values of mole % are based on the amount of raw material (the whole amount of starting materials, i.e. the whole amount including the nitrostilbene derivative represented by the above formula (5) and the trans-isomer thereof, accordingly, in the cases where such a trans-isomer is not included, the amount of nitrostilbene derivative represented by the above formula (5));

Isomer of the raw material: This is the trans-isomer of raw material 5 and is an isomer of nitrostilbene derivative represented by the above formula (5);

MeCN: acetonitrile;
MeOH: methanol;
AcOEt: ethyl acetate;

*1: The detection wavelength is 242 nm; The value in parenthesis indicates the yield (%) to the above, raw material;
*2: A by-product other than the above description (21 area %) was formed;
*3: A condition analogous with that in the Japanese Patent Kokai Publication JP-A-6-172,295 was applied;
*4: A condition analogous with that in J. Am. Chem. Soc., 1940, vol. 62, page 1211 was applied;
*5: A raw material containing 14% of a trans-isomer was used; and
*6: A raw material containing 20% of a trans-isomer was used.

TABLE 1

Examples and Comparative Examples

| Case | Catalyst kind | Catalyst Amt. Mol % | H-donor kind | H-donor amt. mol % | additive kind | additive amt. mol % | raw mtrl. amt. mmol | solvent kind | solvent amt. L/mol | reaction temp □ | reaction time h |
|---|---|---|---|---|---|---|---|---|---|---|---|
| Example 1 | 5% Pt—C | 2 | ammon. formate | 330 | None | — | 25 | MeCN | 4 | 30 | 20.5 |
| Example 2 | 5% Pt—C | 2 | ammon. formate | 300 | None | — | 1.3 | MeCN | 4 | 30 | 19.5 |
| Example 3 (*5) | 10% Pd—C | 2 | ammon. formate | 300 | None | — | 14.5 | MeCN | 4 | 30 | 24 |
| Example 4 (*5) | 10% Pd—C | 2 | ammon. formate | 300 | Aq. Amm. | 100 | 14.5 | MeCN | 4 | 30 | 28 |
| Example 5 | 10% Pd—C | 2 | ammon. formate | 700 | Pyridine | 2 | 0.5 | AcOEt | 15 | 43 | 5 |
| Example 6 | 5% Pt—C | 2 | ammon. formate | 330 | Aq. Amm. | 100 | 25 | MeCN | 4 | 30 | 23 |
| Comp. Ex. 1 (*2 *3) | 5% Pt—C | 2 | hydrogen | excess | None | — | 1.3 | MeCN | 4 | 30 | 3 |
| Comp. Ex. 2 (*4 *6) | $PtO_2$ | 5 | hydrogen | excess | None | — | 2.9 | MeCN | 3.5 | R.T. →55 | 27 |
| Comp. Ex. 3 | 5% Pd—C | 1 | hydrogen | excess | None | — | 1 | MeOH | 10 | R.T. | 16 |
| Comp. Ex. 4 | 5% Ru—C | 2 | hydrogen | excess | None | — | 1.3 | MeCN | 4 | 30 | 20 |

| Case | composition in reaction soln. object 6 | by-product 7 | by-product 8 | by-product 9 | raw mtrl.5 | r.m. isomer |
|---|---|---|---|---|---|---|
| | HPLC area % *1 | | | | | |
| Example 1 | 95 (82) | 3.8 (5.0) | 1.3 (4.3) | 0 (0) | 0 (0) | 0 (0) |
| Example 2 | 86 (82) | 0.9 (1.2) | 0.4 (1.5) | 0.5 (1.8) | 12 (10) | 0 (0) |
| Example 3 (*5) | 69 | 14 | 1.4 | 0.6 | 12 | 1.9 |
| Example 4 (*5) | 72 | 13 | 1.3 | 0.6 | 11 | 1.6 |
| Example 5 | 74 | 7.7 | 7.1 | 6.4 | 3.6 | 0.1 |
| Example 6 | 93 (83) | 5.2 (6.9) | 1.8 (6.5) | 0 (0) | 0 (0) | 0 (0) |
| Comp. Ex. 1 (*2 *3) | 0 | 0 | 79 | 0 | 0 | 0 |
| Comp. Ex. 2 (*4 *6) | 4.9 (2.1) | 69 (42) | 25 (36) | 0 (0) | 0 (0) | 0 (0) |
| Comp. Ex. 3 | 3.6 | 0 | 92 | 0 | 0 | 0 |
| Comp. Ex. 4 | 0 | 0 | 0 | 0 | 100 | 0 |

Effect of the Invention

The present invention enables the possibility to efficiently produce the above described specific aminostilbene derivative. This is important, as the aminostilbene derivate is an active (effective) component of anticancer drugs or intermediates for preparation thereof. The present invention permits the production of aminostilbene derivate by an advantageous method (process) in an environmental condition, as well as permitting safe industrial production. Accordingly, the present invention has significant industrial utility in the fields of pharmaceuticals and the like.

Numerous modifications and variations on the present invention are possible in light of the above teachings. It is, therefore, to be understood that within the scope of the accompanying claims, the invention may be practiced otherwise than as specifically described herein.

What is claimed is:

1. A method for preparing an aminostilbene derivative of formula (2):

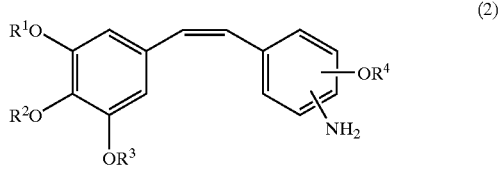

(2)

wherein each of $R^1$, $R^2$, $R^3$ and $R^4$ independently represents an alkyl group having 1–3 carbon atoms and the linking sites of $OR^4$ and $NH_2$ on the benzene ring are optional
  comprising
  reacting a nitrostilbene derivative represented by formula (1) with formic acid and/or a formate salt in the presence of a noble metal catalyst

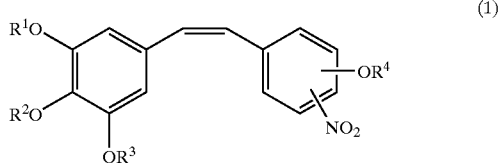

(1)

wherein each of $R^1$, $R^2$, $R^3$ and $R^4$ independently represents an alkyl group having 1–3 carbon atoms and the linking sites of $OR^4$ and $NO_2$ on the benzene ring are optional.

2. The method of claim 1, wherein said aminostilbene derivative is in the form of a salt.

3. The method of claim 1, wherein at least one of $R^1$, $R^2$, $R^3$ and $R^4$ is a methyl group.

4. The method of claim 3, wherein each of the $R^1$, $R^2$, $R^3$ and $R^4$ is respectively a methyl group.

5. The method of claim 1, wherein $OR^4$ is linked at 4-position and the $NO_2$ and $NH_2$ are linked at 3-position on the benzene ring to the linking site of substituted vinyl group.

6. The method of claim 1, wherein the noble metal catalyst is a platinum catalyst or a palladium catalyst.

7. The method of claim 6, wherein the noble metal catalyst is a platinum catalyst.

8. The method of claim 6, wherein the platinum catalyst is platinum on carbon and the palladium catalyst is palladium on carbon.

9. The method of claim 1, wherein the formate salt is ammonium formate.

10. The method of claim 1, wherein the aminostilbene derivative of formula (2) is (Z)-2-methoxy-5-[2-(3,4,5-trimethoxyphenyl)vinyl]aniline or a salt thereof.

11. The method of claim 1, wherein the nitrostilbene derivative represented by formula (1) is (Z)-3,4,4',5-tetramethoxy-3'-nitrostilbene.

12. The method of claim 11, wherein, said reacting is with a formate salt in the presence of a platinum catalyst.

13. The method of claim 6, wherein the aminostilbene derivative of formula (2) is (Z)-2-methoxy-5-[2-(3,4,5-trimethoxyphenyl)vinyl]aniline or a salt thereof.

14. The method of claim 6, wherein the nitrostilbene derivative represented by formula (1) is (Z)-3,4,4',5-tetramethoxy-3'-nitrostilbene.

15. The method of claim 1, wherein the aminostilbene derivative of formula (2) is (Z)-2-methoxy-5-[2-(3,4,5-trimethoxyphenyl)vinyl]aniline or a salt thereof, the nitrostilbene derivative represented by formula (1) is (Z)-3,4,4',5-tetramethoxy-3'-nitrostilbene.

16. The method of claim 1, further comprising isolating the aminostilbene derivative of formula (2) or a salt thereof by a method selected from the group consisting of extraction, crystallization, and chromatography.

17. The method of claim 1, wherein the amount of the noble metal catalyst ranges from 0.1 to 10 mole % to the nitrostilbene derivative represented by formula (1).

18. The method of claim 1, wherein the amount of the formic acid and/or a formate salt ranges from 200–700 mole % to the nitrostilbene derivative represented by formula (1).

19. The method of claim 1, wherein the temperature of the reaction ranges from 0° C. to the boiling temperature of reaction mixture.

20. The method of claim 1, wherein the aminostilbene derivative of formula (2) is (Z)-2-methoxy-5-[2-(3,4,5-trimethoxyphenyl)vinyl]aniline or a salt of the same, the nitrostilbene derivative represented by formula (1) is (Z)-3,4,4',5-tetramethoxy-3'-nitrostilbene, the formic acid and/or a formate salt is a formate salt, and the noble metal catalyst is a platinum catalyst.

21. The method of claim 1, wherein the aminostilbene derivative of formula (2) is (Z)-2-methoxy-5-[2-(3,4,5-trimethoxyphenyl)vinyl]aniline or a salt of the same, the nitrostilbene derivative represented by formula (1) is (Z)-3,4,4',5-tetramethoxy-3'-nitrostilbene, the formic acid and/or a formate salt is a formate salt, and the noble metal catalyst is a palladium catalyst.

* * * * *

UNITED STATES PATENT AND TRADEMARK OFFICE
CERTIFICATE OF CORRECTION

PATENT NO.   : 6,930,205 B2
DATED        : August 16, 2005
INVENTOR(S)  : Takashi Yamamoto et al.

It is certified that error appears in the above-identified patent and that said Letters Patent is hereby corrected as shown below:

<u>Column 6,</u>
Line 3, "oh" should read -- on --.
Line 53, "nitrites" should read -- nitriles --.

Signed and Sealed this

Twenty-eighth Day of February, 2006

JON W. DUDAS
*Director of the United States Patent and Trademark Office*